United States Patent
Kumar et al.

(10) Patent No.: US 9,638,680 B2
(45) Date of Patent: May 2, 2017

(54) COMPOSITION FOR THE COLORIMETRIC DETECTION OF WATER IN HYDROCARBON FUELS AND A PROCESS FOR THE PREPARATION THEREOF

(71) Applicant: Council of Scientific & Industrial Research, New Delhi (IN)

(72) Inventors: Khatri Praveen Kumar, Dehradun (IN); Jain Suman Lata, Dehradun (IN); Ghosh Indrajit Kumar, Dehradun (IN); Umesh Kumar, Dehradun (IN); Chatterjee Alok Kumar, Dehradun (IN); Garg Madhukar Onkarnath, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/594,873

(22) Filed: Jan. 12, 2015

(65) Prior Publication Data
US 2015/0198576 A1    Jul. 16, 2015

(30) Foreign Application Priority Data
Jan. 13, 2014   (IN) .......................... 0093/DEL/2014

(51) Int. Cl.
G01N 33/22    (2006.01)
G01N 33/00    (2006.01)

(52) U.S. Cl.
CPC .................................. *G01N 33/22* (2013.01)

(58) Field of Classification Search
CPC ............................... G01N 33/22; G01N 33/00
USPC ...................................................... 436/40, 39
See application file for complete search history.

(56) References Cited

U.S. PATENT DOCUMENTS

| | | | |
|---|---|---|---|
| 3,041,870 A | 3/1958 | Levine | |
| 2,968,940 A | 1/1961 | Feldman et al. | |
| 3,341,298 A | 9/1967 | Pietrangelo | |
| 3,505,020 A * | 4/1970 | Caldwell | G01N 31/222 436/164 |
| 3,873,271 A | 3/1975 | Young et al. | |
| 4,070,154 A | 1/1978 | Mascher et al. | |
| 4,608,345 A | 8/1986 | Feldman et al. | |
| 4,676,931 A | 6/1987 | Travis | |
| 4,699,885 A * | 10/1987 | Melpolder | G01F 23/04 252/408.1 |
| 6,376,250 B1 * | 4/2002 | Mohtadi | G01N 21/80 252/408.1 |

* cited by examiner

*Primary Examiner* — Christine T Mui
(74) *Attorney, Agent, or Firm* — Brinks Gilson & Lione

(57) ABSTRACT

The embodiments of the present invention disclose a composition for the colorimetric detection of water in hydrocarbon fuels and a process for the preparation thereof. The embodiments of the present invention relate to an improved method for determining the presence or absence of water in non-polar organic fluids such as petroleum oil or hydrocarbon oils by using an indicator system containing a water insoluble wetting agent and a water soluble dye which can be performed rapidly without costly instrumentation and tedious, time consuming analytical methods.

11 Claims, No Drawings

COMPOSITION FOR THE COLORIMETRIC DETECTION OF WATER IN HYDROCARBON FUELS AND A PROCESS FOR THE PREPARATION THEREOF

CROSS REFERENCES TO RELATED APPLICATIONS

This application claims priority under 35 U.S.C. §119 to Indian Application Serial No. 093/DEL/2014, filed on Jan. 13, 2014. The entirety of application 093/DEL/2014 is hereby incorporated by reference herein.

FIELD OF THE INVENTION

The embodiments of the present invention relate to a composition for an improved method for the colorimetric detection of water in hydrocarbon fuels and a process for the preparation thereof. More particularly, the embodiments of the present invention relate to a method for determining the presence or absence of water in non-polar organic fluids such as petroleum oil or hydrocarbon oils by using an indicator system containing a water insoluble wetting agent and a water soluble dye which can be performed rapidly without costly instrumentation and tedious, time-consuming analytical methods.

BACKGROUND OF THE INVENTION

Determination of the presence or absence of water in hydrocarbon fuels is quite important. The adverse effects of excessive water in a fuel system cannot be overstated as ranging from corrosion to poor engine performance, and accordingly over the past 30 years of prior art in the field there have been various methods described for detecting water in hydrocarbon fuels.

For example in U.S. Pat. No. 2,968,940 (1961), Feldman et. al. describes a method to detect 30 parts per million disbursed water in jet aircraft fuels (the "go-no go" limit) by adding one-half gram of a mixture of sodium o-cresolsulfonphthalein and barium carbonate to 100 cc's of jet fuel, shaking it, allowing the powder to settle and noting its color. In U.S. Pat. No. 3,505,020 (1970), Caldwell et. al. discloses an improved mixture of methylene violet or fuchsia (3-amino-7-(dimethylamino)-5-phenylphenazinium chloride) and an absorbent from the Group II metals, such as calcium carbonate, to detect 30 parts per million disbursed water in jet fuels but without reference to the presence or absence of alcohol therein. In U.S. Pat. No. 4,070,154 (1978), Mascher et. al. discloses a colorimetric test for as little as 0.1% alcohol in jet aircraft fuels (the ice formation inhibitors) by an emulsion reagent of sodium vanadiate, 8-hydroxyquinoline, water, acetic acid and an organic solvent. Because water is part of his reagent, it was not intended to detect water in the fuel. In U.S. Pat. No. 4,608,345 (1986), Feldman et. al. describes a colorimetric test for detecting small amounts (1%) of alcohol in gasoline using a variety of alcohol soluble-hydrocarbon insoluble dyes with an absorbent from the Group II metals, such as calcium carbonate; however since the absorbent is non-selective, water must first be removed from the fuel by treating with a drying agent. In U.S. Pat. No. 4,676,931 (1987), the formation of colored hydrates has been described to detect disbursed water in fuels by adding an anhydrous powder which, when shaken with the fuel, would remove only the water so that the presence of alcohol would not interfere with the test. The preferred anhydrous powder was cupric sulfate because it formed two colored hydrated crystals, light blue and dark blue, depending upon the amount of water present, however a few problems were found using this test under actual field conditions. Indian patent 127,617 (1971) provides a device for determining the presence of suspended free water in aviation turbine fuels in concentration as low as 30 ppm. According to this, a composition containing a mixture of ferrous ammonium sulfate and potassium ferricyanide was applied to a filter paper, which was then used for detection of water in hydrocarbon fuels. Presence of water gives green/blue color. Indian patent 127618, 1972 provides a method and device for determining the presence of suspended free water in aviation turbine fuels in concentration as low as 30 ppm. The aforementioned U.S. and Indian patents are hereby incorporated by reference herein.

According to this, a composition containing a mixture of cresol red and barium carbonate in the ratio of 1:100 was used for the detection of free water in the fuel samples. The prepared composition is grayish white in color and packed in the gelatin capsules. Presence of water gives pink color.

The detection methods as mentioned in the prior art are mainly uses the stoichiometric amounts of expensive metal salts, which may produce large excess of metallic waste and thereof are detrimental to the environment. In view of the above problems, it is needed to develop a method for the detection of suspended free water in the hydrocarbon fuels with relatively safe and inexpensive chemicals. The embodiments of the present invention address that need.

SUMMARY OF THE INVENTION

Accordingly, an embodiment of the present invention provides a composition for the colorimetric detection of water in hydrocarbon fuels wherein the said composition comprises a color indicating dye and finely divided clay in the range of 1:50 to 5:1000 wt. % ratio and optionally a metal oxide in the range of 4-50 wt % based on the weight of the total composition. The metal oxide may optionally be present in the range of 4-20 wt %, or in the range of 20-50 wt %, based on the weight of the total composition.

In an embodiment of the present invention, dye is selected from the group consisting of cresol red, sodium salt of o-cresol red, phenol red, and methylene blue.

In one embodiment of the present invention, clay is selected from the group consisting of montmorillonite, montmorillonite KSF, bentonite, and keoline.

In another embodiment of the present invention, metal oxide is selected from the group consisting of BaO, ZnO, CaO, CdO, and MgO.

Still in another embodiment of the present invention, the weight ratio of said finely divided clay, barium oxide to o-cresol red dye is within the range between about 1000:50:5 to 100:20:1.

Still in another embodiment of the present invention, the said composition was prepared by adding dye and finely divided clay and optionally metal oxide.

Still in another embodiment of the present invention, an improved method for the colorimetric detection of water in hydrocarbon fuels using the composition, wherein the method comprises shaking the composition in the test hydrocarbon fuel for a period of 10-15 seconds and then agitating for 1-2 minutes subsequently developing of the intense dark pink color which clearly indicates the presence of free suspended water containing in the test fuel in more or less than 30 ppm.

Still in another embodiment of the present invention, the weight ratio of finely divided clay, color indicating dye and optionally metal oxide in the total composition is in the range between 1000:50:5 to 100:20:1.

Still in another embodiment of the present invention, the method further comprises adding 0.1 to 0.5 g of the composition to 100 ml of a hydrocarbon fuel sample.

DETAILED DESCRIPTION

One objective of the embodiments of the present invention is to provide a composition for an improved method for the colorimetric detection of water in hydrocarbon fuels and a process for the preparation thereof, which obviates the drawbacks of the hitherto known prior art as detailed above.

Another objective of an embodiment of the present invention is to provide an improved composition comprising, a minor proportions of water soluble dye and a major proportion of finally divided naturally occurring clay.

Yet another objective of an embodiment of the present invention is to provide an improved composition comprises cost effective naturally occurring clay selected from the group consisting of K-10, montmorillonite KSF, Bentonite, and combinations thereof.

Yet another objective of an embodiment of the present invention is to provide an improved composition comprising water soluble dye selected from the group consisting of cresol red, phenol red, methylene blue, and gentian violet dye.

Yet another objective of an embodiment of the present invention is to provide a composition comprising of a minor proportion of dye and major proportion of finally divided clay in the range of 1:50 to 5:1000 wt. % ratio.

Yet another objective of an embodiment of the present invention is to provide a cost effective yet environmentally benign composition for detecting the presence of free water in hydrocarbon fuels.

Yet another objective of an embodiment of the present investigation is to provide a method to detect the presence of water in hydrocarbon fuels in the range of 10-50 ppm.

An embodiment of the present invention provides a method for colorimetric detection of water in hydrocarbon fuels, which comprises a mixture of a specific dye and finally divided naturally occurring clay in a weight ratio approximately 1:100 to test hydrocarbons to detect the presence of water. Only small samples of fuel (approx. 5 cc's) need be tested to allow their easy disposal pursuant to environmental concerns, and only small amounts of relatively harmless chemicals comprising a color indicating dye (i.e. cresol red) and finally divided naturally occurring clay (e.g. montmorillonite) are used in the method along with re-usable glass test vials, all of which have no known hazard to the environment. The addition of finally divided group (II) metal oxide such as barium oxide into the above composition of cresol red and clay in the weight ratio 1:20:100 provided improvement in the color detection ability and gave an intense dark pink color in the presence of water in detection fuel. These easily accessible and readily usable reagents, which are stable, storable and can be used under extreme weather conditions make the method ideal for detection of water in the hydrocarbon fuels. A colorimetric reagent is used for detecting water in a finally ground mixture of cresol red, barium oxide and finally divided montmorillonite clay in a weight ratio approx. 1:20:100 to 5:100:1000 for easy detection of water in hydrocarbon fuels. The test for water detection may be carried out under ambient atmospheric conditions in a clear glass vial preferably with screw cap so that approximately 2 cc's of fuel need only be vigorously shaken with approximate 1-2 mg of reagent for production of an intense pink color easily observed in the vial.

The improved sensitivity exhibited by the composition of the embodiments of the present invention makes these reagents especially useful in on-site inspection test for the aviation fuel before the fuel is transferred into the fuel tank of an airplane.

Furthermore, the environmentally benign nature of the naturally occurring clay and its inexpensive nature make the reagents of the embodiments of the present invention ideal for the detection of free suspended water in the hydrocarbon fuels.

The strong visible color of the cresol red dye/BaO/ montmorillonite clay mixtures makes the compounds of the embodiments of the present invention ideal for aviation fuels contained more or less than 30 parts per million of dispersed water. Preferably an intense dark pink color develops when the aviation fuels includes water in an amount of at least 10 ppm, at least 15 ppm, at least 30 ppm, at least 40 ppm, at least 45 ppm, or at least 50 ppm.

EXAMPLES

The following examples are given by way of illustration of the working of the embodiments of the present invention in actual practice and should not be construed to limit the scope of embodiments of the present invention in any way.

Example 1

As indicated previously, the composition of this investigation was discovered after evaluating and testing a large number of dyes and dye-solid combinations. The results of these experiments are given in Table 1. Among the dyes and/or compositions tested, many of them were associated with one or more drawbacks such as poor efficiency, poor color detection, etc., which precluded their use for detecting the presence and extend of dispersed water in hydrocarbon fuels.

TABLE 1

Evaluation of indicators or compositions for use in detecting the water in hydrocarbon fuels.[a]

| Dye | Finely divided solid wetting agent | Indication of color |
| --- | --- | --- |
| Cresol Red | Montmorillonite K-10 | Dark pink |
| Cresol Red | Montmorillonite KSF | Pink |
| Cresol Red | Bentonite | Yellow |
| Cresol Red | Montmorillonite + BaO[b] | Dark intense stable pink |
| Sodium salt of Cresol Red | Montmorillonite + BaO[b] | Intense pink color |
| Phenol Red | Montmorillonite | Pink |
| Sodium salt of Phenol Red | Montmorillonite | Light pink |
| Neutral Red | Montmorillonite | Red |
| Thymbol blue | Montmorillonite | Blue |
| Brilliant yellow | Montmorillonite | yellow |
| Metacresol purple | Montmorillonite | Purple |

[a]A mixture was prepared by adding dye and finely divided clay in 1:100.
[b]The weight ratio of dye, barium oxide and clay that was used as 1:20:100.

Example 2

To show the advantage of the composition and method of the embodiments of the present invention over the existing state of the art methods, sensitivity comparisons were made on various samples which included the composition of the embodiments of the present invention and the prior art compositions used for the detection of free water in hydrocarbon fuels.

In the test, conducted commercial kerosene type jet fuel was used, which was dried prior to use by storing in a container with freshly activated molecular sieves for 48 h. A number of samples were then prepared by adding 15 ppm, 30 ppm and 45 ppm of water to the aviation fuel samples. Different composition of o-cresol red dye/dry montmorillonite clay, cresol red/BaO/montmorillonite clay and phenol red/BaO/montmorillonite clay mixtures were prepared and added to 50 cc portions of the test fuel. Each of the samples was shaken for a period of 10 seconds. After standing for 1-2 minutes, the intensity of the color of the solids was noted. The comparison results are given in Table 2.

greater sensitivity which makes possible the accurate determination of the water content as compared to the utilization of the prior art methods.

TABLE 3

Evaluation of different compositions for use in detecting the water in hydrocarbon fuels.

| Dye | Finely divided solid wetting agent | Indication of color |
|---|---|---|
| Cresol Red | MCM-41 | Yellow orange |
| Cresol Red | Kiselguhr White | No color change |
| Cresol Red | Nano MgO | Light pink |
| Cresol Red | Nano ZnO | Pale yellow |
| Cresol Red | Nano silica (SBA15) | No change |
| Cresol Red | Nano BaO | Pink-Purple |

TABLE 2

Free water detection test by using different amount of the composition

| Composition of indicator mixture | | | | | Grams of indicator mixture per 100 cc of hydrocarbon sample[a] | 2 minute reading Free water | |
|---|---|---|---|---|---|---|---|
| Finely divided solid | | Dye | | | | | |
| Compound | Amt (mg) | Metal oxide | Amt (mg) | Compound | Amt (mg) | | 15 ppm | 40 ppm |
| Montmorillonite | 100 | — | — | Cresol red | 1 | 0.125 | 1 | 3 |
| | | | | | | 0.2 | 3 | 4 |
| Montmorillonite | 100 | BaO | 20 | Cresol red | 1 | 0.2 | >3 | >4 |
| Montmorillonite | 100 | BaO | 20 | Sodium salt of cresol red | 1 | 0.2 | 3 | >4 |
| Montmorillonite | 100 | BaO | 20 | Phenol Red | 1 | 0.2 | 1 | 2 |
| Montmorillonite | 100 | BaO | 20 | Sodium salt of Phenol Red | 1 | 0.2 | 2 | 3 |
| Montmorillonite | 100 | BaO | 20 | Cresol Red | 2 | 0.2 | 4 | >4 |
| Montmorillonite | 100 | — | — | Cresol Red | 3 | 0.2 | 3 | 4 |
| — | — | BaO | 100 | Cresol Red | 3 | 0.2 | >3 | >4 |

Rating scale range 0-5; wherein 0 indicates no visible color change; 1 indicates a poor color; 2 indicates a definite color change and 3, 4, 5 indicates the dark intense color change.
[a] A commercial kerosene type aviation fuel was used as test sample.

Example 3

To show the advantage of the composition and method of the embodiments of the present invention, sensitivity comparisons were made on various samples which included the composition of the embodiments of the present invention and different nanostructured metal oxides such as MgO, ZnO, BaO and mesoporous silica materials, such as MCM-41, for the detection of free water in hydrocarbon fuels.

A number of mixtures consisting of cresol red/MgO, phenol red/MgO, cresol red/ZnO, cresol red sodium salt/ZnO, cresol red/BaO, cresol red sodium salt/BaO, cresol red/MCM-41 mixtures were prepared by using approximately 1:100 weight ratio between dye and finally divided solid. The prepared mixtures (1-2 mg) were added to 50 cc portions of the test fuel. Each of the samples was shaken for a period of 10 seconds. After standing for 2 minutes, the intensity of the color of the solids was noted. The comparison results are given in Table 3. From the results, it can be seen that the color difference afforded by the composition of the embodiments of the present invention is substantially greater than that obtained by the use of other compositions. Such greater color difference with the use of cresol red or its sodium salt and montmorillonite clay mixtures, results in the TABLE 3-continued Evaluation of different compositions for use in detecting the water in hydrocarbon fuels.

| Dye | Finely divided solid wetting agent | Indication of color |
|---|---|---|
| Cresol Red | Nano CaCO$_3$ | Pink |
| Cresol Red | Montmorillonite | Dark Pink |

Example 4

Effect of Weight Ratio of Dye/Clay

A number of mixtures consisting of o-cresol red and montmorillonite clay were prepared by using different weight ratio between dye and finally divided clay. The prepared mixtures (1-2 mg) were added to 50 cc portions of the test fuel. Each of the samples was shaken for a period of 10 seconds. After standing for 1-2 minutes, the intensity of the color of the solids was noted. The comparison results are given in Table 4. From the results, it can be seen that the color difference resulted by the composition i.e. o-cresol red and clay in weight ratio 1:100 is substantially greater than that obtained by the use of other compositions. The addition of BaO to the above mixture of dye and clay enhanced the color detection ability significantly and the resulting mixture provided a dark intense pink color in the presence of water in the detection fuel.

TABLE 4

Evaluation of different compositions for use in detecting the water in hydrocarbon fuels.

| Finally divided solid mixture | Composition | Indication of color |
|---|---|---|
| Cresol Red + clay | 1:50 | Dark pink |
| Cresol Red + clay | 1:100 | Dark pink |
| Cresol Red + clay + BaO | 1:100:20 | Dark intense pink (stable) |
| Cresol Red + BaO | 1:100 | Pink (unstable) |
| Cresol Red + BaO | 1:50 | Pink - purple |

Embodiments of the invention have been described above to illustrate various aspects of the invention, and are not intended to limit the invention to the described embodiments, examples or illustrations. Those skilled in the art may appreciate additional advantages, features and equivalents that are within the scope of the invention as defined by the claims appended hereto.

What is claimed is:

1. A composition for the colorimetric detection of water in hydrocarbon fuels consisting of:
   a color indicating dye,
   finely divided clay in the range of 1:50 to 5:1000 wt. % ratio, and
   optionally, a metal oxide in the range of 4 to 50 wt. %.

2. The composition of claim 1, wherein dye is selected from the group consisting of cresol red, sodium salt of o-cresol red, phenol red, and methylene blue.

3. The composition of claim 1, wherein clay is selected from the group consisting of montmorillonite, montmorillonite KSF, bentonite, and keoline.

4. The composition of claim 1, wherein metal oxide is selected from the group consisting of BaO, ZnO, CaO, CdO, and MgO.

5. The composition of claim 1, wherein the weight ratio of the finely divided clay to the metal oxide, when present in the composition, to the color indicating dye is within the range between about 1000:50:5 to 100:20:1.

6. The composition of claim 1, wherein the composition was prepared by adding the color indicating dye and finely divided clay, and optionally, the metal oxide.

7. An improved method for the colorimetric detection of water in hydrocarbon fuels using the composition of claim 1, wherein the method comprises:
   shaking the composition in the test hydrocarbon fuel for a period of 10-15 seconds, and
   agitating the composition for 1-2 minutes,
   whereby the development of an intense dark pink color indicates the presence of free suspended water contained in the test fuel in an amount of at least 15 ppm.

8. The method of claim 7, wherein the weight ratio of the finely divided clay, to the metal oxide, when present in the composition, to the color indicating dye in the composition is in the range between 1000:50:5 to 100:20:1.

9. The method of claim 7, further comprising adding 0.1 to 0.5 g of the composition of claim 1 to 100 ml of a hydrocarbon fuel sample.

10. The composition of claim 1, wherein the composition is free from a liquid carrier.

11. The method of claim 7, wherein the composition is free from a liquid carrier.

* * * * *